United States Patent

Larkin et al.

Patent Number: 5,098,929
Date of Patent: Mar. 24, 1992

[54] PESTICIDAL COMPOUNDS

[75] Inventors: John P. Larkin, Leighton Buzzard; Ian H. Smith, Eaton Bray, both of England

[73] Assignee: The Wellcome Foundation Limited, London, England

[21] Appl. No.: 478,038

[22] Filed: Feb. 9, 1990

Related U.S. Application Data

[60] Continuation of Ser. No. 189,153, May 2, 1988, abandoned, which is a division of Ser. No. 890,954, Jul. 25, 1986, abandoned.

Foreign Application Priority Data

Jul. 30, 1985 [GB] United Kingdom ............. 8519212
Sep. 12, 1985 [GB] United Kingdom ............. 8522601

[51] Int. Cl.⁵ .................... A01N 43/32; C07D 319/04
[52] U.S. Cl. .................... 514/452; 549/360; 549/363
[58] Field of Search ............. 549/363, 360; 514/452

[56] References Cited

U.S. PATENT DOCUMENTS 4,772,624 9/1988 Palmer et al. .............. 549/363

FOREIGN PATENT DOCUMENTS 152229 8/1985 European Pat. Off.

Primary Examiner—Nicky Chan
Attorney, Agent, or Firm—Nixon & Vanderhye

[57] ABSTRACT

A compound of the formula (I):

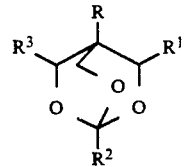

wherein R is $C_{2-10}$ alkyl, alkenyl or alkynyl, each optionally subsituted by or methyl substituted by cyano, $C_{3-4}$ cycloalkyl, halo, $C_{1-4}$ alkoxy or a group $S(O)mR^4$ where $R^4$ is $C_{1-4}$ alkyl and m is 0, 1 or 2, or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)mR^4$ as defined hereinbefore; $R^1$ is halo, $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms, a group $S(O)mR^4$ as defined hereinbefore or alkynyl substituted by tri-$C_{1-4}$ alkylsilyl, or $R^1$ is cyano, spiro-cyclopropyl, gem dimethyl, oxo or methylene optionally substituted by cyano or $C_{1-3}$ alkyl optionally substituted by fluorine, or $R^1$ and R and the carbon atoms to which they are attached form a $C_{5-7}$ carbocyclic ring optionally substituted by halo, $C_{1-3}$ alkyl or alkoxy or $C_{2-3}$ alkenyl, $R^2$ is phenyl, $C_{5-10}$ cycloalkyl or cycloalkenyl each optionally substituted other than phenyl substituted by $C_{2-3}$ alkynyl and $R^3$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo, or $R^3$ is cyano, its use in medicine, pharmaceutical compositions containing it and processes for its preparation.

12 Claims, No Drawings

PESTICIDAL COMPOUNDS

This is a continuation of application Ser. No. 189,153, filed May 2, 1988, now abandoned, which is a divisional of co-pending application Ser. No. 890,754, filed on July 25, 1986, now abandoned.

The present invention relates to novel chemical compounds having pesticidal activity, to methods for their preparation, to compositions containing them and to their use in the control of pests. More particularly the invention relates to a class of 1,3,4-tri-substituted-2,6,7-trioxabicyclo[2,2,2]octanes.

The use of certain 2,6,7-trioxabicyclo[2,2,2]octanes as pesticides is disclosed in European Patent Application No. 152 229; it has now been discovered that derivatives of these compounds having substituents at the 3-position have interesting pesticidal activity.

Accordingly the present invention provides a compound of the formula (I):

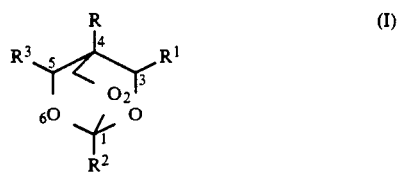

wherein R is $C_{2-10}$ alkyl, alkenyl or alkynyl, each optionally substituted by or methyl substituted by cyano, $C_{3-4}$ cycloalkyl, halo, $C_{1-4}$ alkoxy or a group $S(O)m\ R^4$ where $R^4$ is $C_{1-4}$ alkyl and m is 0, 1 or 2, or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)m\ R^4$ as defined hereinbefore; $R^1$ is halo, $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms, a group $S(O)m\ R^4$ as defined hereinbefore or alkynyl substituted by tri-$C_{1-4}$ alkylsilyl, or $R^1$ is cyano, spiro-cyclopropyl, gem dimethyl, oxo or methylene optionally substituted by cyano or $C_{1-3}$ alkyl optionally substituted by fluorine, or $R^1$ and R and the carbon atoms to which they are attached form a $C_{5-7}$ carbocyclic ring optionally substituted by halo, $C_{1-3}$ alkyl or alkoxy or $C_{2-3}$ alkenyl, $R^2$ is phenyl, $C_{5-10}$ cycloalkyl or cycloalkenyl each optionally substituted, except that $R^2$ is not phenyl substituted by $C_{2-3}$ alkynyl, and $R^3$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo, or $R^3$ is cyano.

Suitably R is propyl, butyl, pentyl, $C_{2-5}$ alkenyl or alkynyl, $C_{5-7}$ cycloalkyl or phenyl each optionally substitued by one to three fluoro, chloro or bromo. Most suitably R is n-propyl, n-butyl, i-butyl, s-butyl, t-butyl, cyclopentyl or cyclohexyl and preferably R is n-propyl, n-butyl, i-butyl, t-butyl or cyclohexyl.

Suitably $R^1$ is cyano, ethynyl or methyl or ethyl optionally substituted by cyano, methoxy, methylthio or fluoro. Most suitably $R^1$ is methyl, cyano, ethynyl, trifluoromethyl or ethyl. Preferably $R^1$ is methyl, trifluoromethyl, cyano or ethynyl.

When $R^2$ is a substituted phenyl, $C_{5-10}$ cycloalkyl or cycloalkenyl group, suitable substituents include halo, cyano, azido, tetrazolyl, a group $SO_2R^5$ wherein $R^5$ is amino or di-$C_{1-4}$ alkylamino, a group $COR^6$ wherein $R^6$ is $C_{1-4}$ alkoxy, benzyloxy, amino or di-$C_{1-4}$ alkylamino, nitro, $C_{1-3}$ alkyl optionally substituted by halo, cyano or alkynyl, or $C_{2-3}$ alkenyl optionally substituted by halo. When $R^2$ is phenyl, $C_{5-10}$ cycloalkyl or cycloalkenyl substituted by an acidic or basic group, salts can be formed of compounds of the formula (I). The present invention includes salts of the compounds of formula (I). The preparation of such salts is carried out by methods well known to those skilled in the art. Typical salts include acid addition salts, such as those from mineral acids, and basic salts, such as those from the alkali earth metals.

Suitably $R^2$ is cyclohexyl, cycloheptyl, cyclooctyl or phenyl optionally substituted at the 3-, 4- and/or 5-position by halo, cyano, azido or nitro and/or at the 2- and/or 6-position by fluoro. Most suitably $R^2$ is cyclohexyl or phenyl optionally substituted at the 3-,4- and/or 5-position by chloro, bromo, iodo, cyano or ethynyl. Preferably $R^2$ is phenyl substituted at the 4-position by chlorine, bromine, ethynyl or cyano.

Suitably $R^3$ is hydrogen or methyl.
Preferably $R^3$ is hydrogen.

Suitable compounds of the formula (I) include those of the formula (IA)

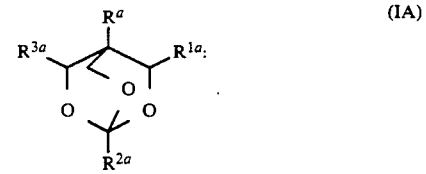

wherein $R^1$ is $C_{2-4}$ alkyl, alkenyl or alkynyl, $C_{5-10}$ cycloalkyl or phenyl, each optionally substituted by cyano or $C_{1-4}$ alkoxy, $R^{1a}$ is cyano or $C_{1-3}$ alkyl, $C_{2-3}$ alkenyl or alkynyl each optionally substituted by cyano, $C_{1-4}$ alkoxy, $C_{1-4}$ alkylthio or halo, $R^{1a}$ is cyano, gem dimethyl or $R^{1a}$ and $R^a$ and the carbon atoms to which they are attached form a $C_{5-7}$ carbocyclic ring optionally substituted by $C_{1-3}$ alkyl or alkoxy; $R^{2a}$ is phenyl, $C_{5-10}$ cycloalkyl or cycloalkenyl each optionally substituted other than phenyl substituted by $C_{2-3}$ alkynyl and $R^{3a}$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo.

Suitably $R^1$ is propyl, butyl, $C_{5-7}$ cycloalkyl or phenyl. Most suitably $R^a$ is n-propyl, butyl, cyclopentyl or cyclohexyl and preferably $R^a$ is propyl, butyl or cyclohexyl.

Suitably $R^{1a}$ is cyano, methyl or ethyl optionally substituted by cyano, methoxy, methylthio or fluoro. Preferably $R^{1a}$ is methyl or ethyl.

Suitable substituents for $R^{2a}$ include halo, cyano, azido, nitro $C_{1-3}$ alkyl optionally substituted by halo or $C_{2-3}$ alkenyl optionally substituted by halo.

Suitably $R^{2a}$ is cyclohexyl, cycloheptyl or phenyl optionally substituted at the 3- or 4-position by halo, cyano, azido or nitro. Most suitably $R^{2a}$ is cyclohexyl or phenyl optionally substituted at the 4-position by chlorine, bromine or cyano.

Preferred compounds of the present invention include
1-(4-bromophenyl)-4-cyclohexyl-3-methyl-2,6,7-trioxabicyclo[2,2,2]octane,
1-(4-chlorophenyl)-3-methyl-4-iso-propyl-2,6,7-trioxabicyclo[2,2,2]octane,
1-(4-bromophenyl)-3-methyl-4-n-propyl-2,6,7-trioxabicyclo[2,2,2]octane, 1-(4-chlorophenyl)-3-methyl-4-n-propyl-2,6,7-trioxabicyclo[2,2,2]octane,
1-cyclohexyl-3-methyl-4-iso-propyl-2,6,7-trioxabicyclo[2,2,2]octane,
1-(4-bromophenyl)-4-t-butyl-3-methyl-2,6,7-trioxabicyclo[2,2,2]octane,
1,4-dicyclohexyl-3-methyl-2,6,7-trioxabicyclo[2,2,2]octane,
4-t-butyl-1-(4-chlorophenyl)-3-methyl-2,6,7-trioxabicyclo[2,2,2]octane.
1-(4-chlorophenyl)-4-n-propyl-3-trifluoromethyl-2,6,7-trioxabicyclo[2,2,2]octane,
1-(4-bromophenyl)-4-n-propyl-3-trifluoromethyl-2,6,7-trioxabicyclo[2,2,2]octane,
1-(4-chlorophenyl)-4-cyclohexyl-3-trifluoromethyl-2,6,7-trioxabicyclo[2,2,2]octane,
1-(4-bromophenyl)-4-cyclohexyl-3-trifluoromethyl-2,6,7-trioxabicyclo[2,2,2]octane,
1-(4-bromophenyl)-3-ethenyl-4-n-propyl-2,6,7-trioxabicyclo[2,2,2]octane,
1-cyclohexyl-4-n-propyl-3-trifluoromethyl-2,6,7-trioxabicyclo[2,2,2]octane,
1-(4-bromophenyl)-3-cyano-4-n-propyl-2,6,7-trioxabicyclo[2,2,2]octane,
1-(4-bromophenyl)-4-cyclohexyl-3-methoxymethyl-2,6,7-trioxabicyclo[2,2,2]octane,
1-cyclohexyl-3-methyl-4-n-propyl-2,6,7-trioxabicyclo[2,2,2]octane,
1-(4-bromophenyl)-4-t-butyl-3-ethyl-2,6,7-trioxabicyclo[2,2,2]octane,
4-t-butyl-1-cyclohexyl-3-methyl-2,6,7-trioxabicyclo[2,2,2]octane,
1-(4-chlorophenyl)3,5-dimethyl-4-n-propyl-2,6,7-trioxabicyclo[2,2,2]octane,
1-(4-bromophenyl)3,5-dimethyl-4-n-propyl-2,6,7-trioxabicyclo[2,2,2]octane,
1cyclohexyl-3,5-dimethyl-4-n-propyl-2,6,7-trioxabicyclo[2,2,2]octane,
1-(4-cyanophenyl)4-n-propyl-3-trifluoromethyl-2,6,7-trioxabicyclo[2,2,2]octane. 4-t-butyl-3-cyano-1-(4-iodophenyl)-2,6,7-trioxabicyclo[2,2,2]octane and
1-(4-bromophenyl)-4-n-butyl-3-methyl-2,6,7-trioxabicyclo[2,2,2]octane,
4-n-butyl-1-(4-chlorophenyl)-3-methyl-2,6,7-trioxabicyclo[2,2,2]octane,
1-(4-bromo-3,5-dichlorophenyl)-4-n-propyl-3-trifluoromethyl-2,6,7-trioxabicyclo[2,2,2]octane,
1-(4-bromo-3-chlorophenyl)-4-n-propyl-3-trifluoromethyl-2,6,7-trioxabicyclo[2,2,2]octane,
Particularly preferred compounds include
1-(4-bromophenyl)-3-methyl-4-n-propyl-2,6,7-trioxabicyclo[2,2,2]octane,
1-(4-bromophenyl)-4-cyclohexyl-3-methyl-2,6,7-trioxabicyclo[2,2,2]octane,
1-(4-chlorophenyl)-3-methyl-4-n-propyl-2,6,7-trioxabicyclo[2,2,2]octane,
1-(4-bromophenyl)-4-t-butyl-3-methyl-2,6,7-trioxabicyclo[2,2,2]octane,
1-(4-chlorophenyl)-4-t-butyl-3-methyl-2,6,7-trioxabicyclo[2,2,2]octane,
1-(4-bromophenyl)-4-n-propyl-3-trifluoromethyl-2,6,7-trioxabicyclo[2,2,2]octane,
1-(4-cyanophenyl)4-n-propyl-3-trifluoromethyl-2,6,7-trioxabicyclo[2,2,2]octane.
1-(4-bromophenyl)-4-n-butyl-3-methyl-2,6,7-trioxabicyclo[2,2,2]octane,
4-n-butyl-1-(4-chlorophenyl)-3-methyl-2,6,7-trioxabicyclo[2,2,2]octane, In a further aspect, the present invention provides a process for the preparation of a compound of the formula (I). The process for the preparation of a compound of the formula (I) may be any method known in the art for preparing analogous compounds, for example by the condensation of a triol of the formula (II) with an orthocarboxylate of the formula $R^2C(OR^7)_3$.

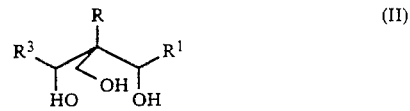

wherein R to $R^3$ are as hereinbefore defined and $R^7$ is $C_{1-4}$ alkyl, phenyl or $C_{7-8}$ aralkyl. Suitably $R^4$ is methyl or ethyl, preferably methyl. The reaction is normally carried out in the presence of an acid such as a mineral acid conveniently hydrochloric acid, or a sulphonic acid derivative, such as toluene sulphonic acid, or an acid resin, or in the presence of a trialkylamine, such as triethylamine, at an elevated temperature, for example between 50° and 200° C., conveniently between 120° and 170° C. The reaction may conveniently be carried out in the absence of a solvent but a suitable solvent may be added if desired.

The triol of the formula (II) may be prepared:

(i) from the corresponding trio where $R^1$ and/or $R^3$ are hydrogen via a protected aldehyde which is reacted with a reagent, such as a Grignard reagent, which is suitable for lengthening the carbon chain followed by deprotection, i.e. as represented in Scheme 1.

In certain cases, it may be convenient to prepare triol derivatives where $R^1$, $R^3$ are hydrogen and one of the hydroxy groups is protected, by reduction of an ester of the formula (III):

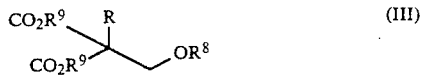

wherein $R^8$ is a protecting group such as benzyl and $R^9$ is $C_{1-4}$ alkyl. This reduction is suitably carried out by a complex hydride such as lithium aluminium hydride in an inert solvent conveniently an ether. The compound of the formula (III) may be prepared from the corresponding compound $RCH(CO_2R^9)_2$ by reaction with a compound $XCH_2OR^8$, wherein X is a leaving group such as a halogen, in the presence of a strong base, such as sodium hydride.

(ii) when it is required to prepare a compound of the formula (I) wherein $R^3$ is hydrogen, by the reduction of a compound of the formula (IV):

wherein R, $R^1$ and $R^9$ are as hereinbefore defined. This reduction is suitably carried out by means of a complex hydride, such as lithium aluminium hydride in an inert solvent such as an ether, for example diethyl ether.

When R and $R^1$ are linked to form a carbocyclic ring, the compound of the formula (IV) is conveniently prepared by the reaction of a compound of the formula (V)

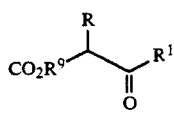

with a compound hal $CO_2R^9$, wherein R, $R^1$, and $R^9$ are as hereinbefore defined and hal is halogen, for example chlorine. This reaction is conveniently carried out in the presence of a Grignard reagent for example ethyl magnesium bromide, in an inert solvent such as an ether, for example tetrahydrofuran. Other compounds of the formula (IV) are conveniently prepared by the reaction of a compound $RCH(CO_2R^9)_2$ with a compound hal $CO.R^1$ wherein R, $R^1$, $R^9$ and hal are as hereinbefore defined or a trifluoroacylating agent such as trifluoroacetic anhydride trifluoroacetic acid or ethyl trifluoroacetate. This reaction is conveniently carried out in the presence of a strong base, such as a metal hydride in a non-polar solvent, for example an aromatic hydrocarbon such as benzene or toluene.

The compounds of the formula (I) may also be prepared by the cyclisation of a compound of the formula (VI)

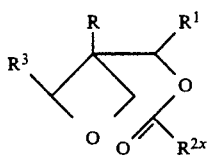

wherein R to $R^3$ are as hereinbefore defined in the presence of an acid catalyst. Boron trifluoride etherate is a particularly preferred acid catalyst for this cyclisation which will normally be carried out in an inert solvent, such as a halogenated hydrocarbon, conveniently dichloromethane, at below ambient temperature, for example between $-100°$ and $0°$ C. and conveniently between $-70°$ and $-50°$ C.

The compounds of the formula (VI) may be prepared by the reaction of compounds of the formula (VII) and (VIII):

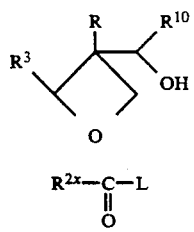

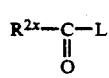

where $R^{10}$ is a group $R^1$ and R to $R^3$ are as hereinbefore defined and L is leaving group such as halo. This reaction conveniently takes place in an inert solvent in the presence of base at a non-extreme temperature. Halogenated hydrocarbons, such as dichloromethane are particularly suitable solvents, pyridine is a preferred base and the reaction will conveniently be carried out at between $-50°$ and $100°$ C., preferably at $0°$ C.

The compounds of the formula (VII) may in turn be prepared from compounds of the formula (II) by reaction with diethyl carbonate in the presence of a strong base, for example potassium hydoxide, in a polar solvent, such as an alcohol, for example ethanol, at an elevated temperature, for example between $50°$ and $100°$ C. This is a preferred method of making compounds of the formula (VII) wherein $R^1=R^{10}=CF_3$.

The compounds of the formula (VII) may alternatively be prepared by the reaction of a Grignard reagent $R^1$ Mg Hal or an $C_{2-4}$ alkynyl lithium compound or sodium oyanide with a compound of the formula (IX)

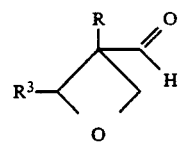

wherein R, $R^1$ and $R^3$ are as hereinbefore defined and Hal is a halogen atom such as bromine or iodine. This reaction is conveniently carried out in an inert solvent, suitably an ether for example diethyl ether or dioxane at a non-extreme temperature, for example between $-50°$ and $50°$ C. and preferably between $-10°$ and $10°$ C. The alkynyl lithium compound is conveniently present as a complex, for example with ethylenediamine. The sodium cyanide is conveniently added as an aqueous solution. The compounds of the formula (IX) may be prepared by oxidation of compounds of the formula (VII) wherein $R^{10}$ is hydrogen by using oxalyl chloride and dimethyl sulphoxide in an inert solvent, such as a halogenated hydrocarbon, for example dichloromethane, followed by a base such as triethylamine or by using pyridinium chlorochromate in an inert solvent, such as a halogenated hydrocarbon, for example dichloromethane.

The compounds of the formula (VII) wherein $R^{10}$ is hydrogen may be prepared in an analogous manner from compounds of formula (II) to the preparation of the compounds of the formula (VII) where $R^{10}$ is trifluoromethyl.

One compound of the formula (I) may be converted to another compound of the formula (I) by methods well known to those skilled in the art. The compounds of Formula (I) may be used to control arthropods such as insect and acarine pests. Thus in a further aspect, the, present invention provides a method of controlling arthropods on animals which comprises the administration of an arthopodially effective amount of a compound of the formula (I) to the animal.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapourising emanator such as a vapourising mat, wettable powder, granule aerosol, emulsifiable concentrate, oil suspensions oil solutions, impregnated article or pour on formulation. Dip concentrates are not applied per se, but diluted with water and the animals immersed in a dipping bath containing the dip wash. Sprays may be applied by hand or by means of a spray race or arch or by means of space spraying machinery. The animal; plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals, plants or surface, as space sprays or aerosols, or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts powder and granules comprise the compound of Formula (I) in intimate admixture with a powdered solid inert carrier for example suitable clays, kaolin, silicone dioxide, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 1 to 90% w/v of the composition and may be selected from kerosene, ketones, alcohols, xylene, aromatic naphtha, aromatic and aliphatic esters and other esters and other solvents known in the formulating art. The concentration of emulsifiers may be varied within wide limits but is preferably in the range of 0.5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Wettable powders and emulsifiable concentrates will normally contain from 1 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body.

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001 to .5% except for undiluted formulations such as pour-on formulations which in general will be deposited at a concentration in the range from 0.1 to 20.0% and preferably 0.1 to 10%.

The compounds of formula (I) are also of use in the protection and treatment of plant species, in which case an effective insecticidal or acaricidal amount of the active ingredient is applied. The application rate will vary according to the compound chosen, the nature of the formulation, the mode of application the plant species, the planting density and likely infestation and other like factors but in general, a suitable use rate for agricultural crops is in the range 0.001 to 3 Kg/Ha and preferably between 0.01 and 1 Kg/Ha. Typical formulations for agricultural use contain between 0.0001% and 50% of a compound of formula (I) and conveniently betwee 0.1 and 15% by weight of a compound of the formula (I).

Particular crops include cotton, wheat, maize, rice, sorghum, soya, vines, tomatoes, potatoes, fruit trees and spruce.

Dusts, greases, pastes, surface and space sprays and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, compounds of formula (I) have activity against other arthropod pests including *Tetranychus urticae Plutella xylostella, Culex* spp. and *Blat-* tella germanica) The compounds of formula (I) are thus useful in the control of arthropods e.g. insects and acarines in any environment where these constitute pests, e.g. in agriculture, in animal husbandry, in public health and in domestic situations.

Insect pests include members of the orders Coleoptera (e.g. Anobium, Tribolium, Sitophilus, Diabrotica, Anthonomus or Anthrenus spp.), Lepidoptera (e.g. Ephestia, Plutella, Chilo, Heliothis, Spodoptera or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma, Liriomyza and Melophagus spp.), Phthiraptera (Malophaga e.g. Damalina spp. and Anoplura e.g. Pediculus humanus capitis, Pediculus humanus humanus, Phythirus pubis Linognathus and Haematopinus spp.), Hemiptera (.e.g Aphis, Bemisia, Aleurodes, Nilopavata, Nephrotetix or Cimes spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.), Siphonaptera (e.g. Ctenocephalides or Pulex spp.), Thysanura (e.g. Lepisma spp.), Dermaptera (e.g. Forficula spp.) and Pscoptera (e.g. Peripsocus spp.).

Acarine pests include ticks, e.g. members of the genera Boophilus, Rhipicephalus, Amblyomma, Hyalomma, Ixodes, Haemaphysalis, Dermocentor and Anocentor, and mites and manges such as Sarcoptes scabiei, and Tetranychus, Psoroptes, Notoedres, Psorergates, Chorioptes and Demodex spp.

Compounds of the invention may be combined with one or more other active ingredients (for example pyrethroids, carbamates and organophosphates) and/or with attractants and/or with fungicides and the like. Furthermore, it has been found that the activity of the compounds of the invention may be enhanced by the addition of a synergist or potentiator, for example: one of the oxidase inhibitor class of synergists, such as piperonyl butoxide or A-O-(2-methylpropyl)O-(2-propynyl)-phenylphosphonate, sometimes abbreviated as NIA 16388; a second compound of the invention; or a pyrethroid pesticidal compound. When an oxidase inhibitor synergist is present in a formula of the invention, the ratio of synergist to compound of Formula (I) will be in the range 25:1-1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:
(a) compounds of Formula (I);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of arthropod pests, such as insect or acarine pests comprising the application to the pest or its environment of a compound of Formula (I);
(f) synergised pesticidal compositions comprising a compound of Formula (I); and
(g) potentiating or non-potentiating mixtures of a compound of Formula (I) and another pesticidal compound;
(h) novel intermediates of the preparation of compounds of Formula (I).

The following Examples illustrate, in a non-limiting manner, preferred aspects of the invention.

The physical data for each of the compounds of the formula (I) is provided in tables after the examples. All indicated temperatures are in °Celsius.

EXAMPLE A

1-Cyclohexyl-4-ethyl-3-methyl-2,6,7-trioxabicyclo[2,2,2]octane (i) Sodium hydride (24 g. 50% dispersion in oil) was added to a stirred solution of diethyl ethylmalonate (94 g.) in dry benzene (300 ml.) at room temperature. The mixture was maintained at 60° C., with stirring, for one hour. The mixture was cooled and acetyl chloride (36 ml.) was added and the reaction mixture was stirred at room temperature for three hours. The reaction mixture was poured into ice and the aqueous mixture was extracted with ether. The ether extracts were washed with water, dried over magnesium sulphate and the solvent was removed in vacuo.

Distillation gave diethyl 2-acetyl-2-ethylmalonate (54 g.), a colourless oil (b.pt. 94° 1.5 m.m.)

Nuclear magnetic resonance spectrum (NMR) was as follows: $^1$H(ppm from TMS in CDCl$_3$, integral, number of peaks, J$_{Hz}$): 4.25, 4H, q, 6; 2.36, 3H, s; 2.2, 2H, m; 1.4, 6H, t, 6; 1.0, 3H, t, 6

(ii) Lithium aluminium hydride (8.0 g.) in dry diethyl ether (200 ml) was stirred at 0°, under a current of dry nitrogen. Diethyl 2-acetyl-2- ethylmalonate (30 g.) in dry ether (50 ml) was added and the mixture was stirred at room temperature for three hours. The mixture was then refluxed, with stirring, for eight hours. A solution of sodium hydroxide (20 g.) and potassium hydrogen phosphate (20 g.) in water (150 ml) was added carefully to the cooled reaction mixture. The pH was adjusted to 5.0 with glacial acetic acid. The solid was removed by filtration and washed with water (20 ml). The combined filtrates and washings were evaporated in vacuo. The residue was washed with acetone (3×100 ml). The acetone washings were evaporated in vacuo. The reside was washed with chloroform (3×100 ml) and the washings were evaporated in vacuo. 2-Ethyl-2-hydroxymethylbutan-1,3-diol was obtained as a pale yellow oil (8.0 g.) Nuclear magnetic resonance spectrum (NMR) was as follows: $^1$H (ppm from TMS in CDCl$_3$, integral, number of peaks, J$_{Hz}$): 4.2, 3H, broad singlet; 4.1, 1H, m; 3.8, 4H, m; 1.4, 5H, m; 1.0, 3H, m.

(iii) Trimethyl orthocyclohexylcarboxylate (1.1 g) was added to 2-ethyl-2-hydroxymethyl-butan-1,3-diol (0.75 g.) One drop of concentrated hydrochloric acid was added and the mixture was maintained at 130° for one hour, under a current of nitrogen. The volatile components were removed in vacuo (3.0 mm.) at 130°.

The residue was purified by chromatography on alumina (Alumina Woelm TSC), eluting with 1:4 dichloromethane: hexane, saturated with ammonia. 1-Cyclohexyl-4-ethyl-3-methyl-2,6,7-trioxabicyclo[2,2,2]octane was obtained as a colourless oil (0.3 g.).

Gas-liquid chromatography (g.l.c.): OV210 at 150° produced one peak.

In an analogous manner, but where appropriate, starting with diethyl n-propylmalonate, diethyl i-propylmalonate or diethyl n-butylmalonate and acetyl chloride, propionyl chloride, butyryl chloride or methoxyacetyl chloride and carrying out the final condensation with trimethyl orthocyclohexylcarboxylate, trimethyl 4-chloro-orthobenzoate or trimethyl 4-bromo-orthobenzoate, the following compounds were prepared:

1-(4-chlorophenyl)-4-ethyl-3-methyl-2,6,7-trioxabicyclo[2,2,2]octane,
1-(4-bromophenyl)-4-ethyl-3-methyl-2,6,7-trioxabicyclo[2,2,2]octane,
1-(4-chlorophenyl)-4-n-propyl-3-methyl-2,6,7-trioxabicyclo[2,2,2]octane,
1-cyclohexyl-4-n-propyl-3-methyl-2,6,7-trioxabicyclo[2,2,2]octane,
1-cyclohexyl-4-i-propyl-3-methyl-2,6,7-trioxabicyclo[2,2,2]octane,
1-(4-bromophenyl)-4-n-propyl-3-methyl-2,6,7-trioxabicyclo[2,2,2]octane,
1-(4-chlorophenyl)-4-i-propyl-3-methyl-2,6,7-trioxabicyclo[2,2,2]octane,
1-(4-bromophenyl)-3-ethyl-4-n-propyl-2,6,7-trioxabicyclo[2,2,2]octane,
1-cyclohexyl-3-ethyl-4-n-propyl-2,6,7-trioxabicyclo[2,2,2]octane,
1-(4-bromophenyl)-3-ethyl-4-i-propyl-2,6.7-trioxabicyclo[2,2,2]octane,
1-(4-bromophenyl)-3-n-propyl-4-i-propyl-2,6,7-trioxabicyclo[2,2,2]octane,
1-cyclohexyl-3-n-propyl-4-i-propyl-2,6,7-trioxabicyclo[2,2,2]octane,
1-(4-bromophenyl)-3-methoxymethyl-4-i-propyl-2,6,7-trioxabicyclo[2,2,2]octane,
1-cyclohexyl-3-methoxymethyl-4-n-propyl-2,6,7-trioxabicyclo[2,2,2]octane,
1-(4-bromophenyl)-3-methoxymethyl-4-n-propyl-2,6,7-trioxabicyclo[2,2,2]octane,
1-cyclohexyl-3-methoxymethyl-4-i-propyl-2,6,7-trioxabicyclo[2,2,2]octan,
1-(4-bromophenyl)-1-cyclohexyl-3-methoxymethyl-2,6,7-trioxabicyclo[2,2,2]octane,
1-(4-bromophenyl)-4-n-butyl-3-methyl-2,6,7-trioxabicyclo[2,2,2]octane,
4-n-butyl-1-(4-chlorophenyl)-3-methyl-2,6,7-trioxabicyclo[2,2,2]octane.

EXAMPLE B:

1-Cyclohexyl-3,4-diethyl-2,6,7-trioxabicyclo[2,2,2]octane (i) 2-Ethyl-2-hydroxymethyl-propan-1,3-diol (34 g.), acetone (37 ml.) and p-toluenesulphonic acid (0.5 g.) were refluxed in benzene (140 ml.) and water was removed using Dean and Stark apparatus. After ten hours refluxing the mixture was cooled and washed with saturated aqueous sodium hydrogen carbonate solution. The benzene solution was dried over anhydrous magnesium sulphate. The solvent was removed in vacuo. Distillation gave 2,2-dimethyl-5-ethyl-5-hydroxymethyl-1,3-dioxane (35 g.), a colourless oil (bpt) 80°-2° 0.9 mm)$^2$.

Nuclear magnetic resonance spectrum (NMR) was as follows: $^1$H (ppm from TMS in CDCl,, integral, number of peaks, $J_{Hz}$): 3.90, 2H, d, 6; 3.85, 4H, s; 3.10, 1H, t, 6; 1.60, 6H, s; 1.55, 2H, m; 1.05, 3H, m.

(ii) 2,2-Dimethyl-5-ethyl-5-hydroxymethyl-1,3-dioxane (33 g.) was added to a stirred suspension of pyridinium chlorochromate (122.6 g.) and anhydrous sodium acetate (7.8 g.) in dry dichloromethane (200 ml.), at 0°, under a current of nitrogen. The mixture was stirred at room temperature for six hours. The mixture was diluted with dry ether (500 ml) and the organic solution was decanted off. The oily residue was treated with ether and the combined extracts were evaporated in vacuo. The residue was purified by chromatography on silica, eluting with ether; hexane 1:3. 2,2-Dimethyl-5-ethyl-5-formyl-1,3-dioxane (30 g.) was obtained as a colourless oil.

Gas-liquid chromatography (g.l.c.): OV210 at 130° produced one peak.

Nuclear magnetic resonance spectrum (NMR) was as follows: $^1$H (ppm from TMS in CDCl$_3$, integral, number of peaks, $J_{Hz}$) 9.6, 1H, s; 4.2, 2H, d, 12; 3.8, 2H, d, 12; 1.4, 8H, m; 0.85, 3H, t, 6.

(iii) A solution of ethyl magnesium bromide (70 ml, 1.3M in tetrahydrofuran) was stirred at 0°, under nitrogen. 2,2-Dimethyl-5-ethyl-5-formyl-1,3-dioxane (10.3 g.) in dry tetrahydrofuran (20 ml.) was added and the mixture was stirred at room temperature for three hours. The mixture was then refluxed, with stirring, for one hour. Saturated aqueous ammonium chloride solution was added to the cooled reaction mixture. The aqueous mixture was extracted with ether. The ether extracts were washed with water, dried over anhydrous magnesium sulphate and the solvent was removed in vacuo. The residue was purified by chromatography on silica gel, eluting with 40% ether hexane. 2,2-Dimethyl-5-ethyl-5-(1-hydroxy propyl)-1,3-dioxane was obtained as a colourless oil (10.0 g.).

Gas-liquid chromatography (g.l.c.): OV210 at 140° produced one peak.

Nuclear magnetic resonance spectrum (NMR) was as follows: $^1$H (ppm from TMS in CDCl$_3$, integral, number of peaks, $J_{Hz}$): 3.70, 5H, m; 2.20, 1H, d, 6; 1.40, 10H m; 1.00, 6H, m.

(iv) 2,2-Dimethyl-5-ethyl-5-(1-hydroxypropyl)-1,3-dioxane (10 g.) and Dowex 50×8−200 ion exchange resin (H$^+$ form) (1.0 g.) in methanol (200ml) containing water (40 ml) was refluxed with stirring for three hours. The mixture was filtered and the filtrate was evaporated in vacuo. 2-Ethyl-2-hydroxymethyl-pentan-1,3-diol (6.0 g.) was obtained as a colourless viscous oil.

Nuclear magnetic resonance spectrum (NMR) was as follows: $^1$H (p.p.m. from TMS in CDCl$_3$, integral, number of peaks, $J_{Hz}$): 3.80, 5H, m; 3.00, 3H, m; 1.8-0.8, 10H, m.

From 2-ethyl-2-hydroxymethyl-pentan-1,3-diol(0.7 g) using the method described in Example A, 1-cyclohexyl-3,4-diethyl-2,6,7-trioxabicyclo[2,2,2]octane (0.3 g.), a colourless oil, was obtained.

Gas-liquid chromatography (g.l.c.): OV210 at 180° produced one peak.

1-(4-chlorophenyl)-3,4-diethyl-2,6,7-trioxabicyclo[2,2,2]octane, was prepared in an analogous manner by substituting trimethyl 4-chloro-orthobenzoate for trimethyl orthocyclohexylcarboxylate in the final condensation.

1-cyclohexyl-4-t-butyl-3-methyl-2,6,7-trioxabicyclo[2,2,2]octane, 1-(4-bromophenyl)-4-t-butyl-3-methyl-2,6,7-trioxabicyclo[2,2,2]octane, 4-t-butyl-1-(4-chlorophenyl)-3-methyl-2,6,7-trioxabicyclo[2,2,2]octane, 1-(4-bromophenyl)-4-t-butyl-3-ethyl-2,6,7-trioxabicyclo[2,2,2]octane were prepared by an analogous approach starting with 2-t-butyl-2hydroxymethyl-propan-1,3-diol.

1-(4-bromophenyl)-3-ethenyl-4-n-propyl-2,6,7-trioxabicyclo[2,2,2]octane was prepared in an analogous manner by substituting vinyl magnesium bromide for ethyl magnesium bromide in step (iii) and substituting triethylamine for hydrochloric acid in step (v)

EXAMPLE C 1-(4-Bromophenyl)-4-cyclohexyl-3-methyl-2,6,7-trioxabicyclo[2,2,2]octane (i) Diethyl cyclohexylmalonate (18.7 g.) was added to a stirred suspension of sodium hydride (4.8 g. 50% dispersion in oil) in dry tetrohydrofuran (50 ml) under nitrogen. The mixture was refluxed, with stirring, for one hour. The mixture was cooled and benzyl chloromethyl ether (13.9 g.) in dry tetrahydrofuran (50 ml) was added and the mixture was refluxed, with stirring, for three hours. The mixture was cooled and poured into water. The aqueous mixture was extracted with ether. The ether extracts were washed with water, dried over anhydrous magnesium sulphate and evaporated in vacuo. Diethyl 2-benzyloxymethyl-2-cyclohexyl-malonate (30 g.) was obtained as a brown oil and was used without further purification.

(ii) Diethyl 2-benzyloxymethyl-2-cyclohexyl-malonate (2 g.) was added to a suspension of lithium aluminium hydride (0.63 g.) in dry ether (30 ml), at 0°, under nitrogen. The mixture was stirred at room temperature for twelve hours. Water (5 ml) was added carefully and the mixture was stirred for ten minutes. 10% sulphuric acid solution (10 ml) was added and the mixture was extracted with ether. The ether extracts were washed with water, dried over anhydrous magnesium sulphate and evaporated in vacuo. The residue was purified by chromatography on silica, eluting with 1:1 ether: hexane. 2-Benzlyloxymethyl-2-cyclohexyl-propan-1,3-diol was obtained as a colourless oil (1.0 g.).

Gas-liquid chromatography (g.l.c.): OV210at 230° produced one peak.

Nuclear magnetic resonance spectrum (NMR) was as follows: $^1$H (ppm from TMS in CDCl$_3$, integral, number of peaks, $J_{Hz}$): 7.35, 5H, s; 4.55, 2H, s; 3.75, 4H, d, 6; 3.60, 2H, s; 2.90, 2H, t, 6; 2.00–0.90, 11H, m.

(iii) 2-Benzyloxymethyl-2-cyclohexyl-propan-1,3-diol(3 g.),2,2-dimethoxypropane (8 ml), p-toluenesulphonic acid (150 mg.) and molecular sieves (type 4A) were heated in refluxing dry toluene (50 ml.) for four hours. The mixture was cooled and filtered. The filtrate was diluted with ether and the ethereal solution was extracted with aqueous sodium hydrogen carbonate solution. The ethereal solution was washed with water, dried over anhydrous magnesium sulphate and evaporated in vacuo. The residue was purified by chromatography on silica, eluting with 1:5 ether:hexane. 5-Benzyloxymethyl-5-cyclohexyl-2,2-dimethyl-1,3-dioxane(3.0 g) was obtained as a colourless oil.

Gas-liquid chromatography (g.l.c.): OV210at 230° produced one peak.

Nuclear magnetic resonance spectrum (NMR) was as follows: $^1$H (ppm from TMS in CDCl$_3$, integral, number of peaks): 7.30, 5H, s; 4.50, 2H, s; 3.70, 4H, s; 3.60, 2H, s; 2.00–0.9, 17H, m.

(iv) 5-Benzyloxymethyl-5-cyclohexyl-2,2-dimethyl-1,3-dioxane (3.0 g.) in dry ether (10 ml.) was added to liquid ammonia (100 ml.) at −70°. Sodium (0.5 g.) was added to the stirred solution. Stirring was maintained at −70°, for one hour. The mixture was then allowed to warm up to −30° and solid ammonium chloride (2.0 g.) was added. The ammonia was removed from the reaction mixture under a current of nitrogen. Water was added and the aqueous mixture was extracted with diethyl ether. The ethereal extracts were washed with water, dried over anhydrous magnesium sulphate and evaporated in vacuo. 5-Cyclohexyl-2,2-dimethyl-5-hydroxymethyl-1,3-dioxane was obtained as a cream solid (2.15 g.) and was used without further purification.

Gas-liquid chromatography (g.l.c.): OV210at 200° produced one peak.

Nuclear magnetic resonance spectrum (NMR) was as follows: $^1$H (ppm from TMS in CDCl$_3$, integral, number of peaks): 3.80, 2H, s; 3.65, 4H, s; 2.30, 1H, s broad; 2.00–0.8, 17H, m.

(v) 5-Cyclohexyl-2,2-dimethyl-5-hydroxymethyl-1,3-dioxane (2.2 g.) was added to a stirred suspension of pyridinium chlorochromate (6.1 g.) and anhydrous sodium acetate (3.0 g.) in dry dichloromethane (50 ml.), at 0°, under a current of nitrogen. The mixture was stirred at room temperature for six hours. The mixture was diluted with dry ether (100 ml) and the organic solution was decanted off. The oily residue was treated with ether and the combined extracts were evaporated in vacuo. 5-Cyclohexyl-2,2-dimethyl-5-formyl-1,3-dioxane was obtained as a pale yellow oil (1.8 g.) and was used without further purification.

Nuclear magnetic resonance spectrum (NMR) was as follows: $^1$H (ppm from TMS in CDCl$_3$, integral, number of peaks, $J_{Hz}$): 9.80, 1H, s; 4.25, 2H, d, 12; 3.90, 2H, d, 12; 2.00–0.8, 17H, m.

Infrared spectrum (1R)(liquid film): $\nu$ 1730 cm.$^{-1.}$ (vi) Methyl magnesium iodide (3.0 ml, 3M solution in ether) was added to a solution of 5-cyclohexyl-2,2-dimethyl-5- formyl-1,3-dioxane (1.8 g.) in dry ether (50 ml.) The mixture was refluxed, with stirring, for two hours, cooled and poured into a mixture of 2N hydrochloric acid solution in ice. The aqueous mixture was extracted with ether. The ether extracts were washed with water, dried over anhydrous magnesium sulphate and evaporated in vacuo. 5-Cyclohexyl-2,2-dimethyl-5-(1-hydroxyethyl)-1,3-dioxane was obtained as a cream solid (1.5 g.)

Gas-liquid chromatography (g.l.c.): OV210at 170° produced one peak.

Nuclear magnetic resonance spectrum (NMR) was as follows: $^1$H (ppm from TMS in CDCl$_3$, integral, number of peaks, $J_{Hz}$): 4.15, 1H, q., 6; 3.90–3.50, 4H, m; 3.10, 1H, s broad; 2.00–0.9, 20H, m.

(vii) 5-Cyclohexyl-2,2-dimethyl-5-(1-hydroxyethyl)-1,3-dioxane (1.5 g.) and Dowex 50×8-200 ion exchange resin (H+ form) (1.0 g.) in methanol (30 ml.) and water (10 ml.) was refluxed with stirring for six hours. The mixture was filtered and the filtrate was evaporated in vacuo. 2-Cyclohexyl-2-hydroxymethyl-butan-1,3-diol was obtained as a pale yellow oil (1.2 g.) and was used without further purification.

Gas-liquid chromatography (g.l.c.): OV210at 160° produced one peak.

Nuclear magnetic resonance spectrum (NMR) was as follows: $^1$H (ppm from TMS in CDCl$_3$, integral, number of peaks, $J_{Hz}$): 4.30, 1H, m; 4.00, 2H, s; 3.95, 2H, s; 3.20, 3H, s broad; 2.00–0.9, 14H, m.

(viii) From 2-cyclohexyl-2-hydroxyethyl-butan-1,3-diol (0.27 g.) and trimethyl 4-bromo-orthobenzoate using the method described in Example A, 1-(4-bromophenyl)-4-cyclohexyl-3-methyl-2,6,7-trioxabicyclo[2,2,2]octane, a colourless solid, was obtained (0.14 g.)

Gas-liquid chromatography (g.l.c.): OV210 at 240° produced one peak.

1,4-Dicyclohexyl-3-methyl-2,6,7-trioxabicyclo[2,2,2]octane was prepared in an analogous manner by substituting trimethyl ortho-cyclohexylcarboxylate for trimethyl 4-bromo-orthobenzoate in the final condensation reaction.

EXAMPLE D 2-(4-Bromophenyl)-4,4a,5,6,7,8,8a-heptahydro 2,4a-epoxymethanobenzo-1,3-dioxin (i) A tetrahydrofuran solution (30 ml) of ethylmagnesium bromide was prepared from bromoethane (7.05 g.) and magnesium (1.5 g.) The solution was cooled to 0° and 2-carbethoxycyclohexanone (10.0 g.) was added carefully. The reaction mixture was stirred at room temperature for 30 minutes and ethyl chloroformate (7.0 g.) was added dropwise, under nitrogen. A white precipitate developed. Sulphuric acid solution (80 ml, 1%) was added and the aqueous mixture was extracted with ether. The ether extracts were washed with dilute aqueous sodium hydrogen carbonate solution, water and then dried over anhydrous magnesium sulphate. The solvent was removed in vacuo. Distillation gave 2,2-dicarbethoxycyclohexanone (7.8 g.), a colourless oil, (b.pt. 98°-102° 0.9 mm.)

Nuclear magnetic resonance spectrum (NMR) was as follows: $^1$H (ppm from TMS in CDCl$_3$, integral, number of peaks, J$_{Hz}$): 4.3, 4H, q.,6; 2.5, 4H, m; 1.8, 4H, m; 1.4, 6H, t, 6.

(ii) A solution of 2,2-dicarbethoxycyclohexanone (3.0 g.) in dry ether (15 ml.) was added dropwise to a stirred suspension of lithium aluminium hydride (1.4 g.) in dry ether (50 ml.) at 0°, under nitrogen. The mixture was refluxed, with stirring, for six hours. Potassium hydroxide (6 g.) in water (100 ml) was added to the stirred mixture. Dipotassium hydrogen phosphate (4.2 g.) and potassium dihydrogen phosphate (3.3 g.) in water (50 ml.) was added. Ether was removed by passing a current of nitrogen through the mixture. The resultant slurry was acidified with glacial acetic acid and the solid was filtered off. The filtrate was evaporated in vacuo. The residue was extracted with acetone and the solution was evaporated in vacuo. 2,2Di-(hydroxymethyl)-cyclohexanol (1.2 g.) was obtained as a pale yellow oil.

Gas-liquid chromatography (g.l.c.): OV210 at 150° produced one peak.

Nuclear magnetic resonance spectrum (NMR) was as follows: $^1$H (ppm from TMS in CDCl$_3$, integral, number of peaks, J$_{Hz}$): 4.6, 3H, s; 4.00-3.70, 5H, m; 1.80-0.9, 8H, m.

(iii) 2,2-Di-(hydroxymethyl)-cyclohexanol (0.76 g.) was added to trimethyl 4-bromo-orthobenzoate (1.1 g.). One drop of concentrated hydrochloric acid was added and the mixture was heated at 140° for three hours. The volatile components were removed in vacuo (3.0 m.m.) at 150°. The residue was purified by chromatography on alumina (alumina Woehm, TSC), eluting with 1:1 dichloromethane:hexane, saturated with ammonia.

2-(4-Bromophenyl)-4,4a,5,6,7,8,8a-heptahydro 2,4a-epoxymethanobenzo-1,3-dioxin was obtained as a colourless solid (0.27 g.)

2-cyclohexyl-4,4a,5,6,7,8,8a-heptahydro 2,4a-epoxymethanobenzo-1,3-dioxin was prepared in analogous manner.

EXAMPLE E 1-(4-Chlorophenyl)-3,5-dimethyl-4-ethyl-2,6,7-trioxabicyclo[2,2,2]octane (i) 2,2-Dimethyl-5-ethyl-5-hydroxymethyl-1,3-dioxane (10 g.) was added to a stirred suspension of sodium hydride (2.4 g., 50% dispersion in oil) in dry tetrahydrofuran (80 ml.) The mixture was refluxed with stirring for one hour. Benzyl chloride (9.2 ml.) was added and the mixture was refluxed with stirring for three hours. the mixture was poured into water and the aqueous mixture was extracted with ether. The ethereal extract was washed with water, dried over anhydrous magnesium sulphate and evaporated in vacuo. 5-Benzyloxymethyl-2,2-dimethyl-5-ethyl-1,3-dioxane was obtained as a pale brown oil (15 g.) and was used without further purification.

(ii) 5-Benzyloxymethyl-2,2-dimethyl-5-ethyl-1,3-dioxane (15.0 g.) and Dowex 50×8-200 ion exchange resin (H+ form) (2.0 g.) in methanol (250ml.) containing water (50 ml.) was refluxed, with stirring, for three hours. The mixture was filtered and the filtrate was evaporated in vacuo. 2-Benzyloxymethyl-2-hydroxymethyl-butan-1-ol was obtained as a yellow oil (9.7 g.).

Nuclear magnetic resonance spectrum (NMR) was as follows: $^1$H (ppm from TMS in CDCl$_3$, integral, number of peaks, J$_{Hz}$): 7.35, 5H, s; 4.55, 2H, s; 3.65, 4H, s; 3.55, 4H, s;1.40, 2H, m; 0.90, 3H, t,6.

(iii) 2-Benzyloxymethyl-2-hydroxymethyl-butan-1ol (9.7 g.) was added to a stirred suspension of pyridinium chlorochromate (9.7 g.) and anhydrous sodium acetate (2.0 g.) in dry dichloromethane (200 ml.) at 0°, under a current of nitrogen. The mixture was stirred at room temperature for six hours. The mixture was diluted with dry ether (200 ml.) and the organic solution was decanted off. The oily residue was treated with ether and the combined extracts were evaporated in vacuo. The residue was purified by chromatography on silica, eluting with 1:2 ether:hexane. 2-Benzyloxymethyl-2-ethyl-propandial was obtained as a pale brown oil (3.3 g.) and was used immediately.

Infrared spectrum (liquid film): $\nu$1720 cm.$^{-1}$ (iv) Methyl magnesium iodide (16 ml. 3M solution in ether) was added to a solution of 2-benzyloxymethyl-2-ethylpropandiol (3.2 g.) in dry ether (70 ml.). The mixture was refluxed, with stirring, for two hours and cooled. Aqueous ammonium chloride solution was added (30 ml., 10%) and the aqueous mixture was extracted with ether. The ethereal extracts were washed with water, dried over anhydrous magnesium sulphate and evaporated in vacuo. The residue was purified by chromatography on silica, eluting with ether. 3-Benzyloxymethyl-3-ethyl-pentan-2,4-diol was obtained as a pale yellow oil (2.1 g.).

Gas-liquid chromatography (g.l.c.): OV210 at 185° produced one peak.

Nuclear magnetic resonance spectrum (NMR) was as follows: $^1$H (ppm from TMS in CDCl$_3$, integral, number of peaks):

7.40, 5H, s; 4.60, 2H, s; 4.40–3.40, 6H, m; 1.60–0.75, 11H, m;

(v) 3-Ethyl-3-hydroxymethyl-pentan-2-4-diol was prepared from 3-benzyloxymethyl-3- ethyl-pentan-2,4-diol using the method described in stage (iv) of example C. 3-Ethyl-3-hydroxymethyl-pentan-2,4-diol was obtained as a pale brown oil.

Gas-liquid chromatography (g.l.c.): OV210 at 170° showed one peak.

Nuclear magnetic resonance spectrum (NMR) was as follows: $^1$H (ppm from TMS in CDCl$_3$, integral, number of peaks): 4.60–3.50, 7H, m; 1.80–0.70, 11H, m.

(vi) 1-(4-Chlorophenyl)-3,5dimethyl-4-ethyl-2,6,7-trioxabicyclo [2,2,2] octane (0.21 g.), a colourless oil, was prepared from 3-ethyl-3-hydroxymethyl-pentan-2,4-diol (0.7 g.) using the method described in stage (iii) of example A.

Gas-liquid chromatography (g.l.c.): OV210 at 220° produced one peak.

In an analogous manner the following compounds were prepared:

1-cyclohexyl-3,5-di-methyl-4-n-propyl-2,6,7-trioxabicyclo[2,2,2]octane, 1-(4-bromophenyl)-3,5-di-methyl-4-n-propyl-2,6,7-trioxabicyclo[2,2,2]octane, 1-(4-chlorophenyl)-3,5-di-methyl-4-n-propyl-2,6,7-trioxabicyclo[2,2,2]octane cl EXAMPLE F 1-(4-Chlorophenyl)-4-n-Propyl-3-trifluoromethyl-2,6,7-trioxabicyclo[2,2,2]octane Sodium hydride (8.0 g 60% dispersion in oil was added to a stirred solution of diethyl n-propylmalonate (40 g.) in dry benzene (200 ml.). The mixture was maintained at 60°, with stirring, for 1 hour. The mixture was cooled and trifluoracetic anhydride (28 ml.) was added carefully. The mixture was stirred at room temperature for 2 hours. Water was added and the aqueous mixture was extracted with diethyl ether. The ethereal extracts were washed with water, dried over anhydrous magnesium sulphate and evaporated in vacuo.

Distillation gave diethyl 2-n-propyl-2-trifluoroacetylmalonate, a colourless oil (b.pt, 73°, 0.2 m.m.) (35 g.).

Gas-liquid chromatography (g.l.c.): OV 210 at 130° produced one peak.

Nuclear magnetic resonance spectrum (NMR) was as follows: $^1$H (ppm from TMS in CDCl$_3$, integral, number of peaks; J$_{H2}$): 4.30, 4H, q, 8; 2.00, 2H, m; 1.50–0.70, 11H, m.

3,3-Di-(hydroxymethyl)-1,1,1-trifluoro-hexan-2-ol was prepared from diethyl 2-n-propyl-2-trifluoroacetylmalonate using the method described for the preparation of 2-ethyl-2-hydroxymethyl-butan-1,3-diol [example A(ii)].

1-(4-Chlorophenyl)-4-n-propyl-3-trifluoromethyl-2,6,7-trioxabicyclo[2,2,2]octane, 1-cyclohexyl-4-n-propyl-3-trifluoromethyl-2,6,7-trioxabicyclo[2,2,2]octane, and 1-(4-bromophenyl)-4-n-propyl-3-trifluoromethyl-2,6,7-trioxabicyclo[2,2,2]octane were prepared from 3,3-di-(hydroxymethyl)-1,1,1-trifluorohexan-2-ol in an analogous method as in Example A (stage (ii).

Using similar methods 1-(4-chlorophenyl)-4-cyclohexyl-3-trifluoromethyl-2,6,7-trioxabicyclo[2,2,-2]octane, 1,4-dicyclohexyl-3-trifluoromethyl-2,6,7-trioxabicyclo[2,2,2]octane and 1-(4-bromophenyl)-4-oxabicyclo[2,2,2]octane and 1-(4-bromophenyl)-4-cyclohexyl-3-trifluoromethyl-2,6,7-trioxabicyclo[2,2,-2]octane were prepared.

By replacing diethyl n-propylmalonate with diethyl prop-2-enylmalonate or diethyl 2-methylprop-2-enylmalonate the following compounds were prepared:

1-(4-bromophenyl)-4-prop-2-enyl-3-trifluoromethyl-2,6,7-trioxabicyclo[2,2,2]octane, 1-cyclohexyl-4-prop-2-enyl-3-trifluoromethyl-2,6,7-trioxabicyclo[2,2,2]octane, 1-(4-bromophenyl)-4-(2-methylprop-2-enyl)-3-trifluoromethyl-2,6,7-trioxabicyclo[2,2,2]octane, 1-cyclohexyl -4-(2-methylprop-2-enyl)-3-trifluoromethyl-2,6,7-trioxabicyclo[2,2,2]octane.

EXAMPLE G 1-(4-Iodophenyl)-4-n-propyl-3-trifluoromethyl-2,6,7-trioxabicyclo[2,2,2]octane (i) A mixture of 3,3-Di-(hydroxymethyl)-1,1,1-trifluorohexan-2-ol (2.8 g.), diethyl carbonate (1.6 ml.), potassium hydroxide (0.1 g) and dry ethanol (4.0 mls) was refluxed gently (oil bath 110°), under a current of nitrogen, for 30 minutes. The ethanol was then removed by distillation. Distillation gave 3-(1-hydroxy-2,2,2-trifluoroethyl)-3-n-propyloxetane (1.7 g.), colourless oil (b.p. 112°, 20–25 m.m.).

Gas-liquid chromatography (g.l.c.): OV 210 at 120° produced one peak.

Infrared spectrum (1R) (liquid film): 3450(s,br), 1300 (s), 1170(s), 1045 (s).

(ii) A solution of 4-iodobenzoyl chloride (2.1 g.) in dry dichloromethane (25 mls) was added to a stirred solution of 3-(1-hydroxy-2,2,2-trifluoroethyl)-3-n-propyloxetane (1.55 g.) and pyridine (1.0 ml.) in dry dichloromethane, at 0°. The reaction mixture was stirred for 24 hours, at room temperature. The mixture was poured into water and the aqueous mixture was extracted with diethyl ether. The ethereal extracts were washed with water, dried over anhydrous magnesium sulphate and evaporated in vacuo. The residue was purified by column chromatography on silica, eluting with 1% triethylamine in hexane.

3-[1-(4-Iodobenzoyloxy)-2,2,2-trifluoroethyl]-3-n-propyloxetane was obtained as a colourless oil (2.4 g.).

Gas-liquid chromatography (g.l.c.): OV 210 at 200° produced one peak.

Nuclear magnetic resonance spectrum (NMR) was as follows: $^1$H (ppm from TMS in CDCl$_3$, integral, number of peaks): 7.70, 4H, m; 4.80–4.20, 5H, m; 2.20–0.80, 7H, m.

(iii) Boron trifluoride etherate (0.54 ml.) was added to a stirred solution of 3-[1-(4-iodobenzoyloxy)-2,2,2-trifluoroethyl]-3-n-propyloxetane (2.3 g.) in dry dichloromethane (50 mls.) at −70°. The mixture was allowed to warm up slowly to room temperature and was then stirred for 12hours. Triethylamine (1.0 ml.) was added and the mixture was poured into water. The aqueous mixture was extracted with diethyl ether. The ethereal extracts were washed with water, dried over anhydrous magnesium sulphate and evaporated in vacuo. The residue was purified by column chromatography on alumina eluting with 1:4 dichloromethane:hexane saturated with ammonia.

1-(4-Iodophenyl)-4-n-propyl-3-trifluoromethyl-2,6,7-trioxabicyclo(2,2,2) octane was obtained as a colourless solid (0.53 g.).

Gas-liquid chromatography (g.l.c.): OV210 at 220° produced one peak.

Nuclear magnetic resonance spectrum (NMR) was as follows: $^1$H (ppm from TMS in CDCl$_3$, integral, number of peaks, J$_{Hz}$): 7.70, 2H, d, 8; 7.30, 2H, d, 8; 4.80–3.80, 5H, m; 1.40, 4H, m; 1.00, 3H, m.

1-(4-Cyanophenyl)-4-n-propyl-3-trifluoromethyl-2,6,7-trioxabicyclo[2,2,2]octane was prepared in an analogous manner by substituting 4-cyanobenzoyl chloride for 4-iodobenzoyl chloride in step (ii)..

1-(4-Bromo-3,5-dichlorophenyl)-4-n-propyl-3-trifluoromethyl-2,6,7-trioxabicyclo[2,2,2]octane and 1-(4-bromo-3-chlorophenyl)-4-n-propyl-3-trifluoromethyl-2,6,7-trioxabicyclo[2,2,2]octane were prepared in analogous manner by substituting 4-bromo-3,5-dichlorobenzoyl chloride and 4-Bromo-3-chlorobenzoyl chloride respectively for 4-iodobenzoyl chloride in step (ii).

By analogous methods, the following compounds were also prepared:

4-n-Butyl-1-(4-bromophenyl)-3-trifluoromethyl-2,6,7-trioxabicyclo[2.2.2]octane 4-n-Butyl-1-(4-iodophenyl)-3-methyl-2,6,7-trioxabicyclo[2.2.2]octane.

4-t-Butyl-3-cyano-1-cyclohexyl-2,6,7-trioxabicyclo[2.2.2]octane.

3-Cyano-1-(4-iodophenyl)-4-n-propyl-2,6,7-trioxabicyclo[2.2.2]octane.

REFERENCES

1. S. M. McElvain and R. E. Stern J. Amer. Chem. Soc., 1955, 77, 4571
2. V. Gash J. Org. Chem., 1972, 37, 2197
3. S. M. McElvain and J. T. Venerable J. Amer. Chem. Soc., 1950, 72, 1661.
4. J. P. Ferris, B. G. Wright and C. C. Crawford J. Org. Chem., 1965, 30, 2367.

TABLE 1

| Number | R$^2$ | R | R$^1$ | R$^3$ | mpt (°C.) | Mass Spectrum Chemical Ionisation M + 1 | Infrared Spectrum | Method of Example |
|---|---|---|---|---|---|---|---|---|
| 1. | 4-Clphenyl | Et | Me | | 48–50 | 269 | 1100(s), 1080(m), 1020(m) | A |
| 2. | 4-Brphenyl | Et | Me | | 53–4 | 313 315 | 1105(s), 1080(w), 1020(s), 1005(w) | A |
| 3. | c.hex. | Et | Me | | oil | 241 | 1080(s), 1010(s), 975(m) | A |
| 4. | 4-Clphenyl | Et | Et | | 73–4 | 283 | 1110(s), 1100(s), 1025(s), 1010(s) | B |
| 5. | c.hex. | Et | Et | | oil | 255 | 1080(s), 1020(s), 970(m) | B |
| 6. | 4-Clphenyl | n-pr | Me | | 39–41 | 283 | 1110(s), 1025(s), 1000(s) | A |
| 7. | 4-Brphenyl | n-pr | Me | | 40 | 327 329 | 1100(s), 1080(w), 1020(s), 1000(m) | A |
| 8. | c.hex | n-pr | Me | | oil | 255 | 1087(s), 1017(s), 975(m) | A |
| 9. | 4-Clphenyl | i-pr | Me | | oil | 283 | 1100(s), 1075(w), 1020(s) | A |
| 10. | c.hex. | i-pr | Me | | oil | 255 | 1090(w), 1055(m), 1020(s), 975(w) | A |
| 11. | 4-Brphenyl | —CH$_2$CH$_2$CH$_2$CH$_2$— | | | Solid | 325 327 | | D |
| 12. | c-hex | —CH$_2$CH$_2$CH$_2$CH$_2$— | | | 43–46 | 253 | 1080(m), 1060(m), 1015(s), 970(s) | D |
| 13. | 4-Brphenyl | c.hex. | Me | | solid | 367 369 | | C |
| 14. | 4-Brphenyl | t-Bu | Me | | 104–113 | 341 343 | 1085(m), 1060(w), 1010(s) | B |
| 15. | 4-Brphenyl | t-Bu | Et | | 122–128 | 355 357 | 1090(m), 1060(w), 1020(s) | B |
| 16. | c.hex | c.hex | Me | | 55–56 | 295 | 1090(m), 1020(s) | C |
| 17. | 4-Clphenyl | Et | Me | Me | oil | 283 | 1105(s), 1080(w), 1025(s), 1000(s) | E |
| 18. | 4-Clphenyl | t-Bu | Me | | 96–98 | 297 | 1140(s), 1100(s), 1025(s) | B |
| 19. | 4-Brphenyl | nPr | CH=CH$_2$ | | solid | 339 341 | 1620(w), 1105(s). 1020(s) | B |
| 20. | c.hex | nPr | CF$_3$ | | 48–49 | 309 | 1170(s), 1140(s), 1090(m), 1030(s) | F |
| 21. | 4-BrPhenyl | nPr | CF$_3$ | | 54–56 | 381, 383 | 1170(s), 1135(m), 1120(m), 1050(m), 1025(m) | F |
| 22. | 4-Clphenyl | nPr | CF$_3$ | | 71–73 | 337 | 1170(s), 1140(m), 1120(m), 1045(s), 1020(s) | F |
| 23. | 4-Brphenyl | c.hex | CF$_3$ | | solid | 421, 423 | 1180(s), 1145(s), 1115(s), 1045(m), 1025(s) | F |
| 24. | 4-Clphenyl | c.hex | CF$_3$ | | solid | 377 | 1170(s), 1100(s), 1120(s) | F |
| 27. | 4-Brphenyl | c.hex | MeOCH$_2$ | | solid | 397, 399 | 1100(s), 1020(s) | A |
| 28. | 4-Iphenyl | nPr | CF$_3$ | | solid | | 1180(s), 1145(s), 1120(s), 1025(s) | G |
| 31. | 4-Iphenyl | nPr | Me | | 58–63° | 375 | 1110(s), 1020(s), 830(s) | H |
| 32. | 4-Brphenyl | nPr | Me | Me | oil | 341, 343 | | E |
| 33. | 4-Clphenyl | nPr | Me | Me | oil | 297 | 1100(s), 1027(s) | E |
| 34. | c.hex | nPr | Me | Me | oil | 269 | 1100(s), 1020(s) | E |
| 35. | 4-Br-phenyl | iPr | nPr | | waxy solid | 355 357 | 1105(s), 1085(m), 1020(s) | A |
| 36. | c.hex | iPr | nPr | | oil | 283 | 1050(m), 1020(s), 980(m) | A |
| 37. | 4CN-phenyl | nPr | CF$_3$ | | solid | 328 | 2250(m), 1170(s), 1140(s), 1110(s), 1050(s), 1015(s) | G |
| 38. | 4-Br-phenyl | 2-methyl-prop-2-enyl | CF$_3$ | | solid | 393 395 | 1185(s), 1065(m), 1110(s), 1020(s), | F |
| 39. | c.hex | 2-methyl-prop-2-enyl | CF$_3$ | | oil | 321 | 1660(w), 1165(s), 1120(m), 1085(m), 1030(m) | F |
| 40. | c.hex | c.hex | CF$_3$ | | solid | 349 | 1180(s), 1100(s), 1030(s) | F |
| 41. | c.hex | prop-2-enyl | CF$_3$ | | oil | 307 | 1650(w), 1180(s), 1140(m), 1090(m), 1030(m) | F |
| 42. | 4-Br-phenyl | prop-2-enyl | CF$_3$ | | solid | 379 381 | 1650(w), 1180(s), 1140(m), 1110(s), 1020(s) | F |
| 43. | c.hex | t-Bu | Me | | 69–71° | | 1055(s), 1025(s) | B |
| 44. | 4-Br-phenyl | n-pr | Et | | solid | 341 343 | 1105(s), 1032(s), 1020(s) | A |
| 45. | c.hex | n-pr | Et | | oil | 269 | 1090(m), 1062(m), 1020(s) | A |
| 46. | 4-Br-phenyl | i-pr | Et | | oily solid | 341 343 | 1110(m), 1020(s) | |
| 47. | 4-Br-phenyl | n-pr | MeOCH$_2$ | | solid | 357 359 | 1110(m), 1020(s) | A |
| 48. | c,hex | n-pr | MeOCH$_2$ | | oil | 285 | 1105(m), 1080(m), 1020(s) | A |
| 49. | 4-Br-phenyl | i-pr | MeOCH$_2$ | | solid | 357 359 | 1140(m), 1100(s), 1000(s) | A |
| 50. | c.hex | i-pr | MeOCH$_2$ | | oil | 285 | 1100(s), 1055(s), 1025(s) | A |
| 51. | 4-Br-phenyl | n-Bu | Me | | solid | 341 343 | 1100(s), 1010(s), 990(m) | A |
| 52. | 4-Cl-phenyl | n-Bu | Me | | | 297 | 1095(s), 1015(s), 990(m) | A |

TABLE 1-continued

| | | | | | | |
|---|---|---|---|---|---|---|
| 58. | 4-Br-3,5-di-cl-phenyl | n-pr | $CF_3$ | | solid | 449 451 |
| 59. | 4-Br-3-cl-phenyl | n-pr | $CF_3$ | | solid | 415 417 |
| 60. | 4-Br-phenyl | n-Bu | $CF_3$ | | 50–52° | 395–397 |
| 61. | 4-I-phenyl | n-Bu | Me | | solid | |
| 62. | c.hex | t-Bu | CN | | oil | |
| 63. | 4-I-phenyl | n-Pr | CN | | solid | | c.hex = cyclohexyl
t-Bu = tertiary butyl
n-Pr = normal propyl
i-Pr = iso propyl

Nuclear Magnetic Resonance Spectrum [$^1$H carried out in $CDCl_3$ and expressed as ppm from TMS,
Number   number of protons, number of peaks, $J_{Hz}$-(where appropriate)].

1. 7.55, 2H, d, 8; 7.30, 2H, d, 8; 4.50–3.80, 5H, m; 1.70–1.90, 5H, m; 0.95, 3H, t, 6.
2. 7.45, 4H, s; 4.4–4.0, 5H, m; 1.7–1.2, 5H, m; 0.9, 3H, t, 6
3. 4.00, 5H, m; 2.00–0.6, 19H, m
4. 7.50, 2H, d, 8; 7.30, 2H, d, 8; 4.1–3.8, 5H, m; 2.0–0.8, 10H, m
5. 3.90, 5H, m; 2.0–0.9, 21H, m
6. 7.40, 2H, d, 8; 7.65, 2H, d, 8; 4.4–3.9, 5H, m; 1.7–0.9, 10H, m
7. 7.40, 4H, s; 4.50–4.00, 5H, m; 1.40, 3H, d, 6; 1.30, 4H, m; 1.00, 3H, m
8. 4.25–3.6, 5H, m; 2.00–0.8, 21H, m
9. 7.50, 2H, d, 7; 7.25, 2H, d, 7; 4.5–4.00, 5H, m; 1.80–1.20, 4H, m; 0.95, 6H, d, 6.
10. 4.25, 1H, q, 6; 4.0, 4H, s; 2.00–0.8, 21H, m.
11. 7.40, 4H, s; 4.55, 1H, dd, 8, 3; 4.00, 4H, m; 2.20–0.90, 8H, m
12. 4.35, 1H, dd, 7, 3; 3.80, 4H, m; 2.2–0.8, 19H, m.
13. 7.40, 4H, s; 4.55, 1H, q, 6; 4.15, 4H, s; 2.00–0.80, 14H, m.
14. 7.40, 4H, s; 4.60–4.00, 5H, m; 1.55, 3H, d, 6; 1.00, 9H, s.
15. 7.40, 4H, s; 4.40–4.00, 5H, m; 2.00, 2H, m; 1.20, 3H, t, 6; 1.00, 9H, s
16. 4.30, 1H, q, 6; 4.00, 4H, s, 2.20–0.80, 25H, m.
17. 7.45, 2H, d, 8; 7.20, 2H, d, 8; 4.40, 2H, q, 6; 4.00, 2H, m; 1.30, 8H, m; 0.90, 3H, m.
18. 7.40, 2H, d, 8; 7.20, 2H, d, 8; 4.80–3.80, 5H, m; 1.60, 3H, d, 7; 1.00, 9H, s
19. 7.50, 4H, s; 6.20–5.20, 1H, m; 4.60, 2H, m; 4.30–3.90, 5H, m; 1.40–0.70, 7H, m.
20. 4.60–3.60, 5H, m; 2.20–0.80, 18H, m.
21. 7.50, 4H, m; 4.80–3.80, 5H, m; 1.70–0.80, 7H, m.
22. 7.45, 2H, d, 8; 7.35, 2H, d, 8; 4.60–3.80, 5H, m; 1.60–0.80, 7H, m.
23. 7.50, 4H, s; 4.70, 1H, m; 4.20, 4H, m; 2.00–0.90, 11H, m.
24. 7.50, 2H, d, 8; 7.30, 2H, d, 8; 4.80, 1H, m; 4.30, 4H, m; 2.00–0.90, 11H, m
27. 7.50, 4H, s; 4.80–3.50, 10H, m; 2.20–1.00, 11H, m.
28. 7.40, 2H, d, 8; 7.30, 2H, d, 8; 4.70–3.80, 5H, m; 1.40, 4H, m; 1.00, 3H, m.
31. 7.70, 2H, d, 8; 7.30, 2H, d, 8; 4.5–3.9, 5H, m; 1.45, 3H, d, 6; 1.7–0.8, 7H, m.
32. 7.50, 4H, s; 4.50–3.50, 4H, m; 1.70–0.80, 13H, m.
33. 7.45, 2H, d, 8; 7.35, 2H, d, 8; 4.50–3.90, 4H, m; 1.50–1.10, 10H, m; 0.90, 3H, m.
34. 4.30–3.70, 4H, m; 2.00–1.00, 21H, m; 0.90, 3H, m.
35. 7.40, 4H, s; 4.40–4.00, 5H, m; 2.00–0.75, 14H, m.
36. 4.30–3.70, 5H, m; 2.20–0.70, 25H, m.
37. 7.65, 4H, s; 4.80–3.80, 5H, m; 1.75–0.80, 7H, m.
38. 7.50, 4H, s; 5.05, 1H, s; 4.80, 1H, s; 4.60–4.00, 5H, m; 2.30, 1H, d, 14; 2.20, 1H, d, 14; 1.75, 3H, s.
39. 4.95, 1H, s; 4.72, 1H, s; 4.40–3.70, 5H, m; 2.17, 1H, d, 14; 2.07, 1H, d, 14; 1.90–0.90, 14H, m.
40. 4.60–3.80, 5H, m; 2.00–0.80, 22H, m.
41. 5.65, 1H, m; 5.15, 2H, m; 4.60–3.75, 5H, m; 2.35–0.90, 13H, m.
42. 7.50, 4H, s; 5.65, 1H, m; 5.20, 2H, m; 4.60–4.00, 5H, m; 2.40–2.10, 2H, m.
43. 4.40–3.80, 5H, m; 2.0–0.95, 23H, m.
44. 7.40, 4H, s; 4.20–3.80, 5H, m; 1.70, 2H, m; 1.40–0.90, 10H, m.
45. 4.00–3.75, 5H, m; 2.00–0.80, 23H, m.
46. 7.40, 4H, s; 4.20, 5H, m; 1.80, 3H, m; 1.30, 3H, m; 1.00, 6H, d, 6
47. 7.40, 4H, s; 4.40–4.00, 5H, m; 3.80, 2H, d; 3.40, 3H, s; 1.40. 4H, m; 1.00, 3H, m.
48. 4.40–4.00, 5H, m; 3.80, 2H, d; 3.55, 3H, s; 2.20–1.00, 18H, m.
49. 7.40, 4H, s; 4.50, 1H, m; 4.20, 4H, s; 3.80, 2H, d, (broad), 3.40, 3H, s; 2.00 1H, m; 1.00, 6H, dd.
50. 4.30, 1H, m; 4.00, 4H, m; 3.65, 2H, m; 3.40, 3H, s; 2.00–0.80, 18H, m
51. 7.50, 4H, s; 4.50–3.90, 5H, m; 1.50–0.90,12H, m
58. 7.60, 2H, s; 4.50, 1H, m; 4.35, 1H, m; 4.10, 3H, m; 1.60–0.85, 7H, m.
59. 7.70, 1H, d, 1.5; 7.60. 1H, d, 7; 7.35, 1H, dd, 7, 1.5; 4.50, 1H, m; 4.35, 1H, m; 4.05, 3H, m; 1.60–0.80, 7H, m.
60. 7.50, 4H, s; 4.50, 1H, m; 4.35, 1H, m; 4.05, 3H, m; 1.50–0.80, 9H, m.
61. 7.70, 2H, d, 7; 7.40, 2H, d, 7; 4.60–4.00, 5H, m; 1.80–0.80, 12H, m.
62. 4.75, 1H, d; 4.30–3.75, 4H, m; 1.85–1.50, 6H, m; 1.20–1.00, 5H, m; 0.95, 9H, s.
63. 7.70, 2H, d; 7.30, 2H, d; 4.90, 1H, d; 4.35–4.05, 4H, m; 1.45–1.15, 4H, m; 0.95, 3H, t.

BIOLOGICAL ACTIVITY

The compound number refers to the numbers allocated to the compounds in the table spanning pages 41 to 44.

A. Lethal activity against House flies

The activity of compounds of the invention against unanaesthatised female *Musca domestica* (WRL strain), was demonstrated by the topical application to the test insect of a solution of the compound under test in butanone.

The activity of the test compound was also assessed when applied topically in conjunction with a synergist [6μg piperonyl butoxide (PB) per insect]. Mortality was assessed after 24 and 48 hours.

The following compounds were active at less than 30 μg/fly:
1,11,12,15,16,19,20,22,37,38,40,41,42,44,45,46,47,48,49,-50,17,32,33,34.

The following compounds were active at less than 1 μg/fly: 6,7,8,9,10,13,14,18,21,23,24,27

B. Lethal Activity Against *Blattella germanica*

The activity of oompounds of the invention against unanaesthatised male *Blatella germanica* (WRL strain) was demonstrated by the topical application to the test insect of a solution of the compound under test in butanone.

The activity of the test compound was assessed when applied topically in conjunction with a synergist [10μg piperonyl butoxide (PB) per insect]. Mortality was assessed after 24 and 48 hours.

The following compounds were active at less than 50 μg/insect: 1,5,11,12,13,15,18,19,20,21,23,27,36,37,38,39,40,41,42,4-4,48,32,33,34.

The following compounds were active at less than 5 μg/insect: 6,7,8,9,29,30.

C. Lethal Activity Against *Sitophilus granarius*

The activity of the compounds of the invention against S.granarius adults was demonstrated by addition of the compound in acetone solution to grain, to which the insects were later infested. Mortality was assessed after 6days The following compounds gave activity at less than 200 ppm solution of acetone: 16,18,19,20,22,23,27,37,41,42,43,44,32,33,34.

The following compounds gave activity at less than 50 ppm solution of acetone: 6,14,15,21.

D. Lethal activity against *Culex quinquefasciatus*

The activity of the compounds of the invention against female Culex adults was demonstrated by direct spraying of 0.5 ml of compound in OPD/Methylene chloride. Mortality was assessed after 24 hours.

The following compounds were active at less than 1.0%. 6,12,14,15,18,19,21,22,23,24,27,37,39,41,43,44,48,50,33.

E. Mammalian Toxicity

Compound 15 has an LD$_{50}$ value of greater than 20 mg/Kg when given orally to mice (Charles River CD1).

| Formulations | | |
|---|---|---|
| 1. | Emulsifiable Concentrate | |
| | Compound 11 | 10.00 |
| | Ethylan KEO | 20.00 |
| | Xylene | 67.50 |
| | Butylated Hydroxyanisole | 2.50 |
| | | 100.00 |
| 2. | Wettable Powder | |
| | Compound 11 | 25.0 |
| | Attapulgite | 69.50 |
| | Sodium isopropylbenzene sulphonate | 0.50 |
| | Sodium salt of condensed naphthalene sulphonic acid | 2.50 |
| | Butylated hydroxytoluene | 2.50 |
| | | 100.00 |
| 3. | Dust | |
| | Compound 11 | 0.50 |
| | Butylated Hydroxyanisole | 0.10 |
| | Talc | 99.40 |
| | | 100.00 |
| 4. | Bait | |
| | Compound 11 | 40.25 |
| | Icing Sugar | 59.65 |
| | Butylated hydroxy toluene | 0.10 |
| | | 100.00 |
| 5. | Lacquer | |
| | Compound 11 | 2.5 |
| | Resin | 5.0 |
| | Butylated Hydroxy anisole | 0.5 |
| | High aromatic white spirit | 92.0 |
| | | 100.00 |
| 6. | Aerosol | |
| | Compound 11 | 0.30 |
| | Butylated Hydroxy anisole | 0.10 |
| | 1,1,1-Trichloroethane | 4.00 |
| | Odourless Kerosene | 15.60 |
| | Arcton 11/12. 50:50 mix | 80.00 |
| | | 100.00 |
| 7. | Spray | |
| | Compound 11 | 0.1 |
| | Butylated Hydroxy anisole | 0.1 |
| | Xylene | 10.0 |
| | Odourless Kerosene | 89.8 |
| | | 100.00 |
| 8. | Potentiated Spray | |
| | Compound 11 | 0.1 |
| | Piperonyl Butoxide | 0.5 |
| | Butylated Hydroxyanisole | 0.1 |
| | Xylene | 10.1 |
| | Odourless Kerosene | 89.2 |
| | | 100.0 |

We claim:
1. A compound of the formula:

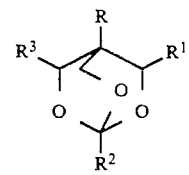

wherein R is $C_{2-4}$ alkyl, $C_{2-4}$ alkenyl, $C_{2-4}$ alkynyl, $C_{5-10}$ cycloalkyl, phenyl, $C_{2-4}$ alkyl substituted by cyano or $C_{1-4}$ alkoxy, $C_{2-4}$ alkenyl substituted by cyano or $C_{1-4}$ alkoxy, $C_{2-4}$ alkynyl substituted by cyano or $C_{1-4}$ alkoxy, $C_{5-10}$ cycloalkyl substituted by cyano or $C_{1-4}$ alkoxy, or phenyl substituted by cyano or $C_{1-4}$ alkoxy;

$R^1$ cyano, $C_{2-3}$ alkenyl, $C_{2-3}$ alkynyl, $C_{1-3}$ alkyl substituted by cyano, $C_{1-4}$ alkoxy, $C_{1-4}$ alkylthio or halo, $C_{2-3}$ alkenyl substituted by cyano, $C_{1-4}$ alkoxy, $C_{1-4}$ alkythio or halo, or $C_{2-3}$ alkynyl substituted by cyano, $C_{1-4}$ alkoxy, $C_{1-4}$ alkylthio or halo, or $R^1$ and R and the carbon atoms to which they are attached form a $C_{5-7}$ carbocyclic ring or $R^1$ and R and the carbon atoms to which they are attached from a $C_{5-7}$ carbocyclic ring substituted by $C_{1-3}$ alkyl or $C_{1-3}$ alkoxy;

$R^2$ phenyl, phenyl substituted by halo, cyano, azido, nitro, $C_{1-3}$ alkyl or $C_{1-3}$ alkyl substituted by halo; $C_{5-10}$ cycloalkyl, $C_{5-10}$ cycloalkyl substituted by halo, cyano, azido, nitro, $C_{1-3}$ alkyl, $C_{2-3}$ alkenyl, $C_{1-3}$ alkyl substituted by halo or $C_{2-3}$ alkenyl substituted by halo; or $C_{5-10}$ cycloalkenyl, $C_{5-10}$ cycloalkenyl substituted by halo, cyano, azido, nitro, $C_{1-3}$ alkyl substituted by halo or $C_{2-3}$ alkenyl substituted by halo;

$R^3$ is hydrogen, $C_{2-3}$ alkenyl, $C_{2-3}$ alkynyl, $C_{1-3}$ alkyl substituted by cyano, $C_{1-4}$ alkylthio, $C_{1-4}$ alkoxy or halo, $C_{2-3}$ alkenyl substituted by cyano, $C_{1-4}$ alkylthio, $C_{1-4}$ alkoxy or halo or $C_{2-3}$ alkynyl substituted by cyano, $C_{1-4}$ alkylthio, $C_{1-4}$ alkoxy or halo.

2. A compound according to claim 1 in which R is n-propyl, n-butyl, i-butyl, n-butyl, t-butyl, cyclopentyl or cyclohexyl.

3. A compound according to claim 1 in which $R^1$ is trifluoromethyl, cyano or ethynyl.

4. A compound according to claim 1 in which $R^2$ is phenyl substituted at the 4-position by chlorine, bromine or cyano.

5. A compound according to claim 4 in which $R^3$ is hydrogen.

6. A compound according to claim 1, in which $R^2$ is phenyl substituted by halo, cyano, azido, nitro, $C_{1-3}$ alkyl, $C_{1-3}$ haloalkyl, $C_{2-3}$ alkenyl or $C_{2-3}$ haloalkenyl, $C_{5-10}$ cycloalkyl substituted by halo, cyano, azido, nitro, $C_{1-3}$ alkyl, $C_{1-3}$ haloalkyl, $C_{2-3}$ alkenyl or $C_{2-3}$ haloalkenyl, or cycloalkenyl substituted by halo, cyano, azido, nitro, $C_{1-3}$ alkyl, $C_{1-3}$ haloalkyl, $C_{2-3}$ alkenyl or $C_{2-3}$ haloalkenyl.

7. A compound according to claim 1, in which $R^2$ is cyclohexyl, cycloheptyl, phenyl or phenyl substituted at the 3-, 4- or 5- position by halo, cyano, azido or nitro.

8. An insecticidal or acaricidal formulation comprising a compound of claim 1 in admixture with a carrier or diluent.

9. A mixture of a compound of claim 1 and another pesticidal compound selected from a pesticidal pyrethroid, carbamate or an organophosphate, or an attractant or fungicide.

10. A pesticidal composition comprising a compound of claim 1, together with an oxidase inhibiting amount of an oxidase inhibitor, a second compound of claim 19 or a pyrethroid pesticidal compound.

11. A method for the control of arthropod pests comprising the application to the pest or its environment of an arthropodially affective amount of a compound of claim 1.

12. 1-(4-Bromo-3,5-dichlorophenyl)-4-n-propyl-3-trifluoromethyl-2,6,7trioxabicyclo[2,2,2]octane.

* * * * *